(12) United States Patent
Kim et al.

(10) Patent No.: US 10,881,763 B2
(45) Date of Patent: Jan. 5, 2021

(54) CLOSED LOOP GRANULAR JAMMING APPARATUS

(71) Applicant: BUCKNELL UNIVERSITY, Lewisburg, PA (US)

(72) Inventors: Charles John Kim, Lewisburg, PA (US); Paden Michael Troxell, Curwensville, PA (US); Kaixiang Shi, Columbus, OH (US)

(73) Assignee: BUCKNELL UNIVERSITY, Lewisburg, PA (US)

( * ) Notice: Subject to any disclaimer, the term of this patent is extended or adjusted under 35 U.S.C. 154(b) by 0 days.

(21) Appl. No.: 16/399,011

(22) Filed: Apr. 30, 2019

(65) Prior Publication Data

US 2019/0328937 A1    Oct. 31, 2019

Related U.S. Application Data

(60) Provisional application No. 62/664,434, filed on Apr. 30, 2018.

(51) Int. Cl.
*A61B 17/02* (2006.01)
*A61B 17/30* (2006.01)
(Continued)

(52) U.S. Cl.
CPC .......... *A61L 31/14* (2013.01); *A61B 17/0293* (2013.01); *A61B 17/30* (2013.01);
(Continued)

(58) Field of Classification Search
CPC ........ A61L 31/14; A61L 31/005; A61L 31/06; A61L 34/30; A61B 17/0293; A61B 17/30;
(Continued)

(56) References Cited

U.S. PATENT DOCUMENTS 8,282,545 B1 * 10/2012 Bodenstein ............ A61B 1/313
600/205
8,475,074 B1 * 7/2013 Henry ....................... B32B 3/26
148/563

(Continued)

FOREIGN PATENT DOCUMENTS

| KR | 101456102 B1 | 11/2014 |
| WO | 2011130475 A2 | 10/2011 |
| WO | 2018084869 A1 | 5/2018 |

*Primary Examiner* — Pedro Philogene
(74) *Attorney, Agent, or Firm* — McNees Wallace & Nurick LLC (57) ABSTRACT

A closed loop granular jamming apparatus is disclosed including a three-dimensional membrane structure filled with granular material. Fluid is evacuated from the structure which induces a jamming effect, whereas the viscosity of the granular media increases with increasing particle density. The thin membrane conforms to the shape of the granular material. Decreasing enclosed volume and increasing packing density prevents particles from distributing within the confined space, inducing the aggregate to behave as a solid. In the jammed state, the apparatus is resistive to force and change of shape. The apparatus is returned to the unjammed state by releasing the vacuum. The size and shape of the apparatus may be repeatedly adjusted by alternating between the jammed and unjammed states. The closed loop granular jamming apparatus may include toroidal and cylindrical shapes with articulating inserts and compliant spines.

24 Claims, 6 Drawing Sheets

(51) Int. Cl.
*A61L 31/00* (2006.01)
*A61L 31/02* (2006.01)
*A61L 31/06* (2006.01)
*A61L 31/14* (2006.01)
*A61B 34/30* (2016.01)
*A61B 90/00* (2016.01)
*A61B 17/00* (2006.01)

(52) U.S. Cl.
CPC ............ *A61B 34/30* (2016.02); *A61L 31/005* (2013.01); *A61L 31/026* (2013.01); *A61L 31/06* (2013.01); *A61B 2017/00557* (2013.01); *A61B 2017/00946* (2013.01); *A61B 2017/0212* (2013.01); *A61B 2090/0817* (2016.02)

(58) Field of Classification Search
CPC ........... A61B 2017/00557; A61B 2017/00946; A61B 2017/0212; A61B 2090/0817
USPC ................................................ 600/201–220
See application file for complete search history.

(56) References Cited

U.S. PATENT DOCUMENTS

| | | | |
|---|---|---|---|
| 8,548,626 B2* | 10/2013 | Steltz | B25J 15/0023 |
| | | | 294/192 |
| 8,727,410 B2 | 5/2014 | Jones et al. | |
| 9,764,220 B2 | 9/2017 | Keating et al. | |
| 10,661,446 B2* | 5/2020 | Hurwit | B25J 9/1697 |
| 2016/0106508 A1* | 4/2016 | Lathrop | A61B 90/14 |
| | | | 606/130 |
| 2018/0296424 A1 | 10/2018 | Parra et al. | |

* cited by examiner

CLOSED LOOP GRANULAR JAMMING APPARATUS

RELATED APPLICATIONS

This application claims the benefit of and priority to U.S. Prov. App. No. 62/664,434 entitled "Closed Loop Granular Jamming Apparatus," filed Apr. 30, 2018, which is hereby incorporated by reference in its entirety.

FIELD OF THE INVENTION

The present invention is directed to a closed loop granular jamming apparatus. More particularly, the present invention is directed to a closed loop granular jamming apparatus including a three-dimensional membrane structure filled with granular material.

BACKGROUND OF THE INVENTION

Prior devices for holding an object or multiple objects may lack sufficient degrees of freedom to securely grip the object or multiple objects in arbitrary configurations. Existing robotic grippers that utilize granular jamming may not achieve force closure. Existing granular jamming apparatuses that consist of spherical or ellipsoidal geometry for gripping or joint-locking do not sufficiently change and hold shape or resist force while preserving access and visibility for circumferential retraction of openings such as incisions in thyroidectomy or abdominal surgery. A granular jamming apparatus that does not suffer from one or more of the above drawbacks would be desirable in the art.

BRIEF DESCRIPTION OF THE INVENTION

This disclosure pertains to general devices that utilize the granular jamming phenomena with a looped enclosure structure. The devices are comprised of flexible enclosures with a general toroidal geometry. The enclosures are filled with granular materials, such that when vacuum is applied to the devices, they transition from a very flexible, fluid-like state to one that is very rigid. As described below, the devices may also include rigid and flexible inserts that contact the granular media to effectively transmit load. Additionally, the devices may also include flexible spines to bias the overall shape of the device.

In an exemplary embodiment, a closed loop granular jamming apparatus includes a membrane fashioned in a three-dimensional, closed loop geometry which is mathematically defined by a genus g surface where g is greater than or equal to one, a granular material deposited within an enclosed space of the membrane, and a port providing a source of fluid egress and ingress from and to the enclosed space.

Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are exemplary closed loop granular jamming apparatuses. Embodiments of the present disclosure, in comparison to jamming apparatuses not utilizing one or more features disclosed herein, increases gripping, increases joint locking, increases hold, increases force resistance, increases adjustability for holding an object in arbitrary configurations, or combinations thereof.

The present invention provides a novel closed loop granular jamming apparatus, including a three-dimensional membrane structure filled with granular material and a port for fluid ingress and egress from and to the enclosed space.

The novel granular jamming apparatus relies upon a membrane structure fashioned in a three-dimensional, closed loop geometry, which is mathematically defined by a genus g surface where g is greater than or equal to one. Existing granular jamming apparatuses consist of hemispherical, spherical or ellipsoidal geometry, which are mathematically defined as genus-0 surfaces. This novel closed loop granular jamming apparatus uniquely relies on mathematical genus g surfaces where g is greater than or equal to one, such as a torus, which is a genus-1 surface. In simpler terms, the novel closed loop granular jamming apparatus includes bodies with one or more holes, whereas existing granular jamming bodies have no holes.

The present closed loop granular jamming apparatus passively exists in a deformable, unjammed state and transitions to a rigid, jammed state when fluid is evacuated from the granule-filled membrane structure. The evacuation of fluid from the structure induces a jamming effect, whereas the viscosity of the granular media increases with increasing particle density. The thin membrane conforms to the shape of the granular material. Decreasing enclosed volume and increasing packing density prevents particles from distributing within the confined space, inducing the aggregate to behave as a solid. In the jammed state, the apparatus is resistive to force and change of shape. The apparatus is returned to the unjammed state by releasing the vacuum. The size and shape of the apparatus may be repeatedly adjusted by alternating between the jammed and unjammed states.

In contrast to existing granular jamming apparatuses that consist of spherical or ellipsoidal geometry for gripping or joint-locking, the present closed loop granular jamming apparatus permits a change of shape or resist force while preserving access and visibility through the body. This apparatus is suitable for applications where such function is desired, such as retracting and retaining an opening, holding instruments, or clamping while permitting visibility and access. For example, the novel closed loop granular jamming apparatus is suitable for use in surgical retraction, such as in thyroidectomy, where the edges of tissue surrounding an incision or wound must be retracted and retained while permitting visibility and access for surgical instruments.

Figure 1:
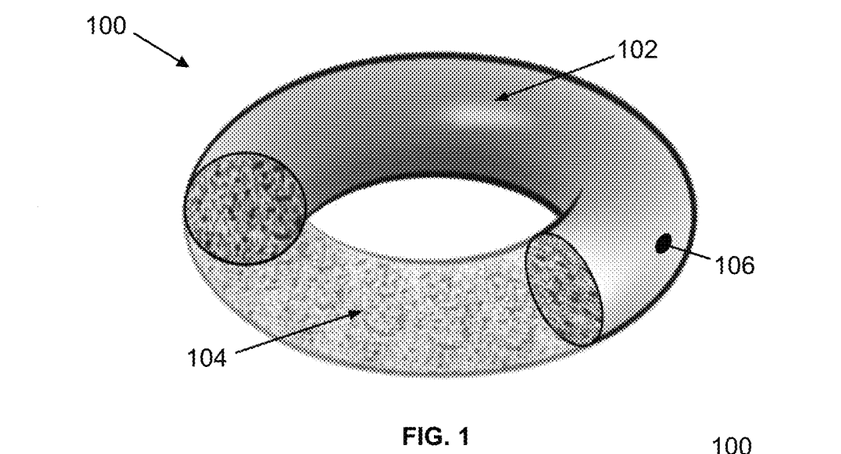
FIG. 1 is a rendered cutaway view of an exemplary closed loop granular jamming apparatus, according to an embodiment of the present disclosure.

Referring now to FIG. 1, a rendered cutaway view of an exemplary closed loop granular jamming apparatus 100 is shown. The novel apparatus of FIG. 1 is somewhat similar in operating principle to conventional granular jamming apparatuses, such as universal robotic grippers, in that it includes a deformable membrane filled with granular material, and further in that the apparatus may be transitioned to a jammed state by evacuation of fluid from within the granule-filled membrane body. However, such conventional apparatuses are of hemispherical, spherical or ellipsoidal geometry and are primarily used for gripping and releasing objects with irregular surfaces or locking mechanical joints, all of which tend to make them unsuitable for use in the context of retracting or retaining an opening, clamping, or holding objects while preserving visibility and access, such as in surgical retraction.

Figure 2:
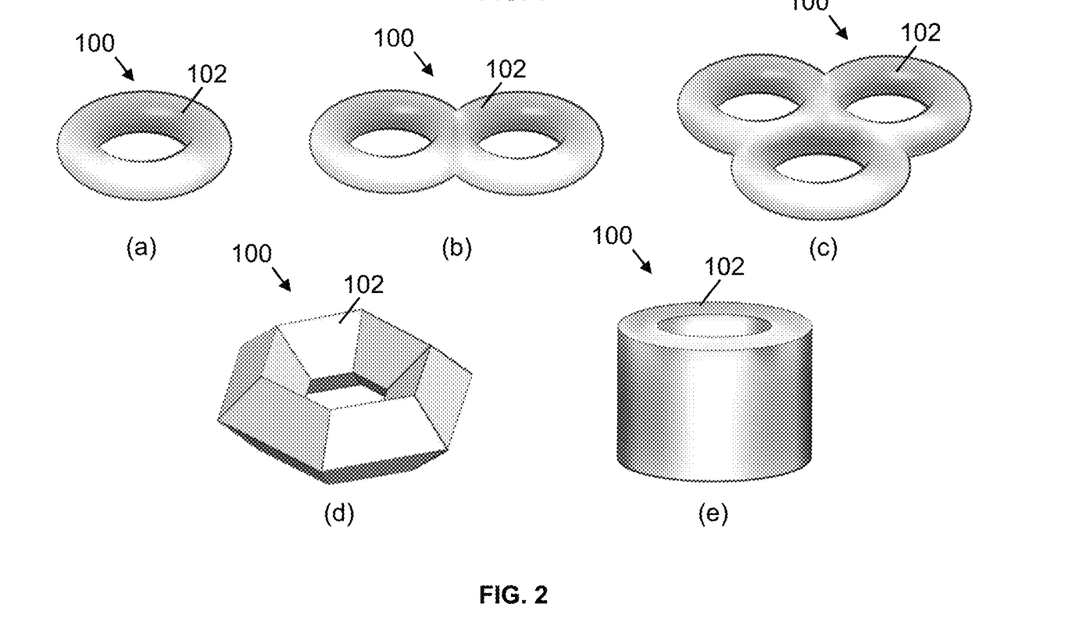
FIG. 2 is a rendered perspective projection view of various exemplary embodiments of closed loop granular jamming apparatuses, including: (a) a torus; (b) a genus-2 surface; (c) a genus-3 surface; (d) a toroidal polyhedron; and (e) a right circular hollow cylinder, according to an embodiment of the present disclosure.

Accordingly, the apparatus 100 of FIG. 1 includes a deformable membrane 102 fashioned in a three-dimensional, closed loop geometry which is mathematically defined by a genus g surface where g is greater than or equal to one, a granular material 104 deposited within the enclosed space of the membrane, and a port 106 providing the source of fluid egress and ingress from and to the enclosed space. The embodiment depicted in FIG. 1 is a torus, which is mathematically defined as a genus-1 surface, however, the apparatus 100 may be formed with membranes fashioned in genus g surfaces where g is greater than or equal to one. Examples of various geometric embodiments are shown in FIG. 2, which include, but are not limited to, a torus (a), genus-2 surface (b), genus-3 surface (c), toroidal polyhedron (d), and right circular hollow cylinder (e).

Further, the apparatus 100 of FIG. 1 includes a deformable membrane 102 fashioned in a three-dimensional, closed loop geometry which may be made of any flexible material such as, but not limited to, an elastomeric material, a polymer, a polyester film, a coated cloth, and combinations thereof. The granular material 104 deposited within the enclosed space of the membrane 102 may include one or any mixture of any organic or inorganic solid compound ground into small granules, including, but not limited to, plastics, metals, glasses, woods, coffees, nuts, seeds, or combinations thereof. The fluid (not shown) surrounding the granular material 104 may be a gas or liquid, which is evacuated and returned via one or more ports 106. Fittings and ports 106 for fluid ingress and egress may contain filters to separate the granular material 104 from the moving fluid.

Figure 3:
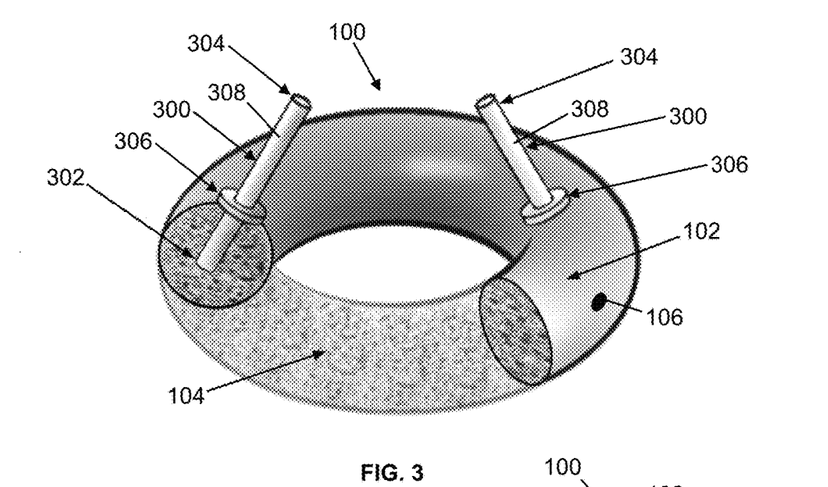
FIG. 3 is a rendered cutaway view of another exemplary closed loop granular jamming apparatus which includes in articulating insert, according to an embodiment of the present disclosure.

Referring now to FIG. 3, a rendered cutaway view of another exemplary closed loop granular jamming apparatus 100 is shown, which includes articulating inserts 300. The general embodiment is shown in FIGS. 1 and 2 with the addition of at least one insert 300 including a proximal end 302 and a distal end 304, wherein the proximal end 302 is positioned internal of the apparatus membrane 102 and surrounded circumferentially by granules 104, and the distal end 304 is located external of the apparatus membrane 102 and is exposed to the ambient environment.

The embodiment present in FIG. 3 is a torus, which is mathematically defined as a genus-1 surface, however, further embodiments include all embodiments of the apparatus with membranes fashioned in genus g surfaces where g is greater than or equal to one. Examples of various geometric embodiments are shown in FIG. 4, include, but are not limited to, a torus (a), genus-2 surface (b), genus-3 surface (c), toroidal polyhedron (d), and right circular hollow cylinder (e).

Figure 4:
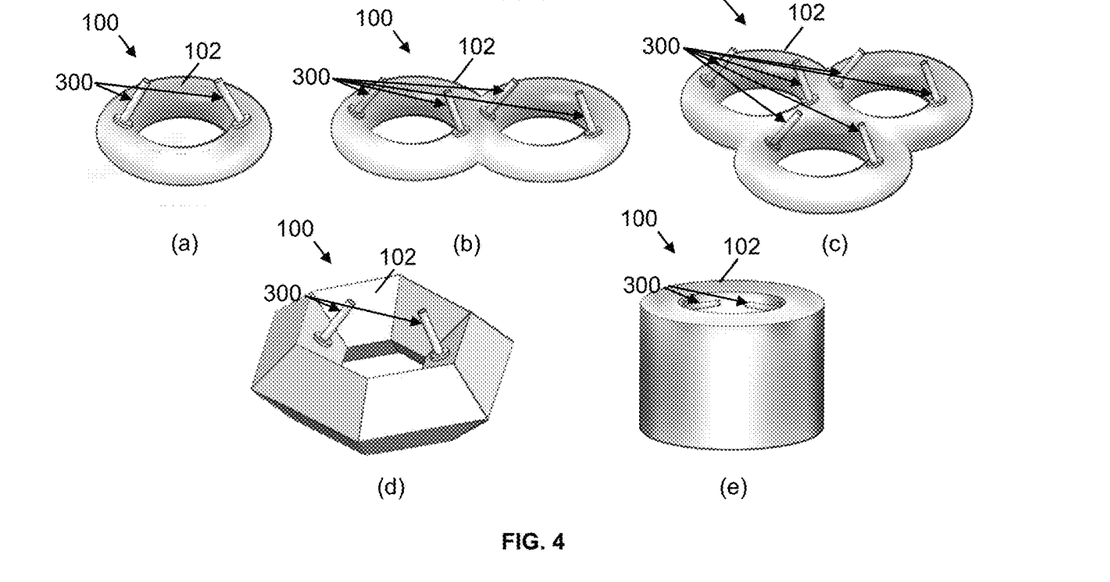
FIG. 4 is a rendered perspective projection view of various exemplary embodiments of closed loop granular jamming apparatuses include articulating inserts, including: (a) a torus; (b) a genus-2 surface; (c) a genus-3 surface; (d) a toroidal polyhedron; and (e) a right circular hollow cylinder, according to an embodiment of the present disclosure.
Figure 5:
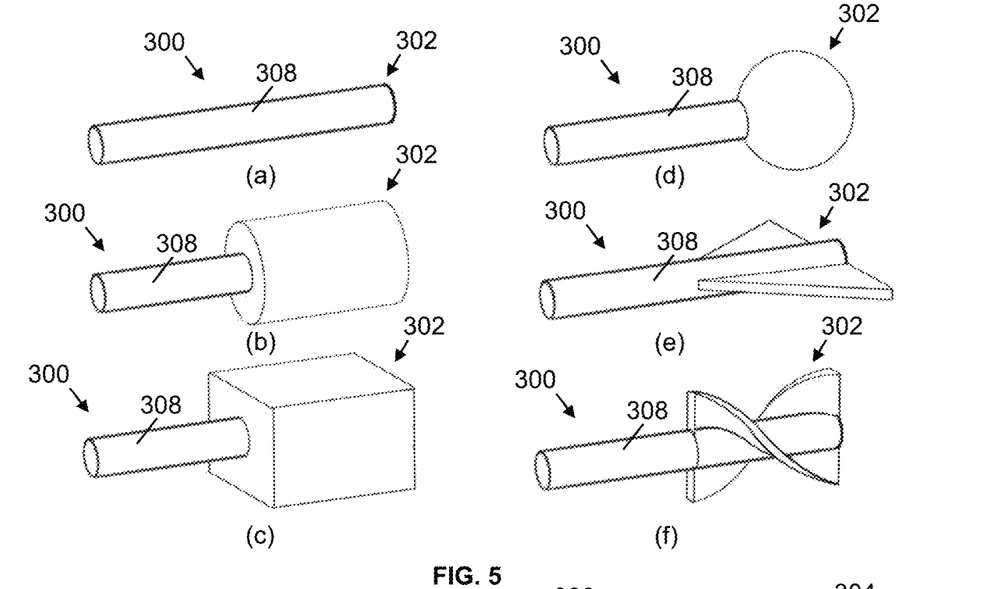
FIG. 5 is a perspective projection view of various exemplary embodiments of the proximal end of articulating inserts, including: (a) a straight shaft; (b) a cylinder; (c) a rectangular prism; (d) a sphere; (e) a finned shaft; and (f) a screw, according to an embodiment of the present disclosure.
Figure 6:
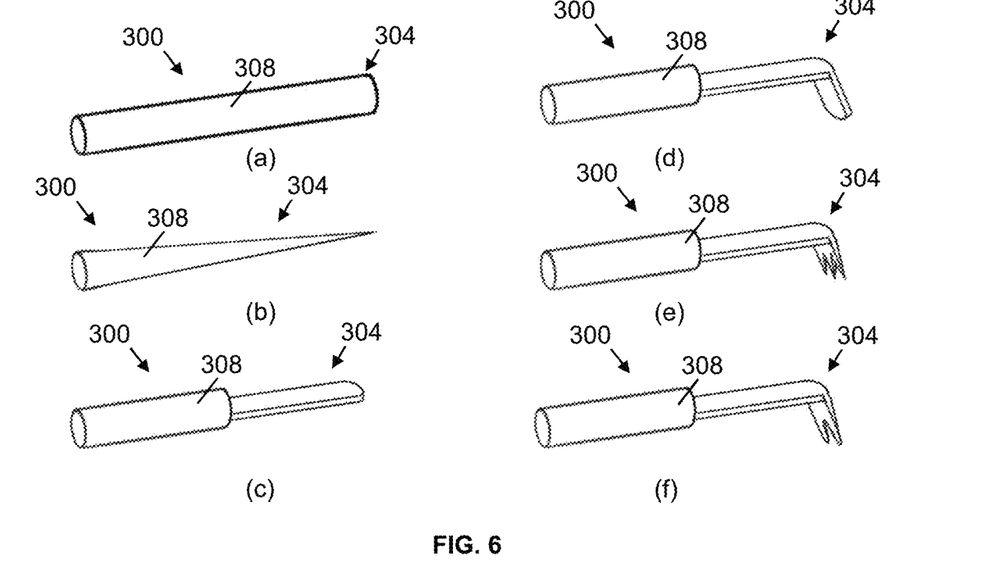
FIG. 6 is a perspective projection view of various exemplary embodiments of the distal end of articulating inserts, including: (a) a straight shaft; (b) a tapered shaft (also referred to as a probe); (c) a spatula; (d) a flat blade retractor; (e) a sharp finger retractor; and (f) a blunt finger retractor, according to an embodiment of the present disclosure.

This general embodiment of FIG. 3 includes one or more exemplary inserts 300, however the embodiments shown in FIGS. 3 and 4 include two such inserts 300. The insert 300 is coupled to the membrane with an evacuable sealing relationship such that the membrane 102 is molded around the insert 300 or the insert 300 is connected to the membrane 102 via a seal or gasket 306. The proximal end 302 of an exemplary insert 300 is positioned internal of the apparatus membrane 102 and includes a shaft 308 and a cross-sectional geometry. The cross-sectional geometry may include, but is not limited to, an ellipse, a circle, a triangle, a rounded triangle, a quadrilateral, a rounded quadrilateral, a rectangle, a rounded rectangle, a square, a rounded square, a trapezoid, a rounded trapezoid, a parallelogram, a rounded parallelogram, a rhombus, a rounded rhombus, a pentagon, a rounded pentagon, a star, a rounded star, or combinations thereof. Examples of various geometric embodiments of the proximal end 302 of the insert 300 are shown in FIG. 5, including, but not limited to, a shaft (a), a cylinder (b), a rectangular prism (c), a sphere (d), a finned shaft (e), a screw (f), a right cylinder, an oblique cylinder, a circular cylinder, an elliptical cylinder, a triangular prism, a rounded triangular prism, a rounded rectangular prism, a spheroid, or combinations thereof. The distal end 304 of an exemplary insert 300 is positioned external of the apparatus membrane 102 and includes a shaft 308 and a cross-sectional geometry. The cross-sectional geometry may include, but is not limited to, an ellipse, a circle, a triangle, a rounded triangle, a quadrilateral, a rounded quadrilateral, a rectangle, a rounded rectangle, a square, a rounded square, a trapezoid, a rounded trapezoid, a parallelogram, a rounded parallelogram, a rhombus, a rounded rhombus, a pentagon, a rounded pentagon, a star, a rounded star, or combinations thereof. Examples of various geometric embodiments of the distal end 304 of the insert 300 are shown in FIG. 6, including, but not limited to, a shaft (a), a tapered shaft (also referred to as a probe) (b), a spatula (c), a flat blade retractor (d), a sharp finger retractor (e), a blunt finger retractor (f), or combinations thereof. The exemplary insert 300 may be made of any suitable material, including, but not limited to, a metal, a plastic, an acrylonitrile butadiene styrene (ABS), a polylactic acid (PLA), an acetal, a polyamide, an acrylic, a polycarbonate, a polyurethane, or combinations thereof. Additional embodiments of the insert 300 may include modular construction wherein the proximal end 302 is removable and replaceable by a twist lock, screw, snap fit, magnet, or combinations thereof.

Figure 7:
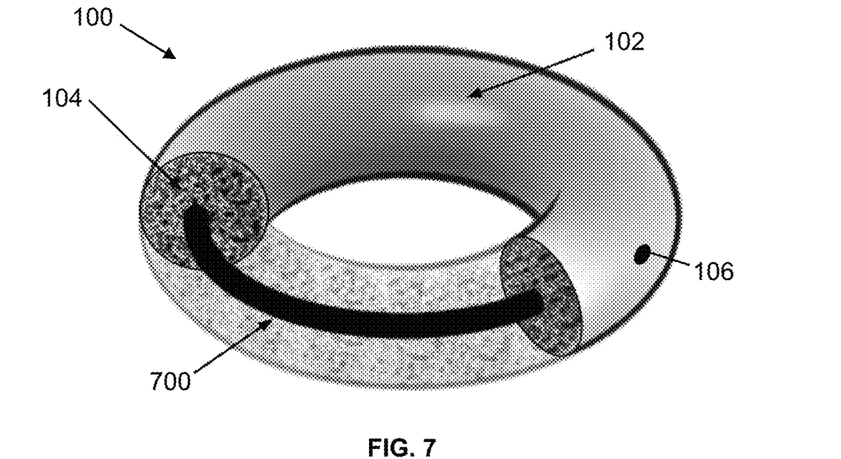
FIG. 7 is a rendered cutaway view of another exemplary closed loop granular jamming apparatus which includes a compliant spine, according to an embodiment of the present disclosure.

Referring now to FIG. 7, a rendered cutaway view of another exemplary closed loop granular jamming apparatus 100 is shown, which includes a compliant spine 700. The general embodiment is shown in FIGS. 1 and 2 with the addition of at least one compliant spine structure 700 positioned internally within the apparatus 100 and surrounded circumferentially by granules 104.

The general embodiment present in FIG. 7 is a torus, which is mathematically defined as a genus-1 surface, however, further embodiments include all embodiments of the apparatus 100 with membranes 102 fashioned in genus g surfaces where g is greater than or equal to one. Examples of various geometric embodiments are shown in FIG. 2, including a torus (a), genus-2 surface (b), genus-3 surface (c), toroidal polyhedron (d), and right circular hollow cylinder (e). The spine structure may include a three-dimensional, closed loop geometry which is mathematically defined by a genus g surface where g is equal to that of the apparatus 100.

This general embodiment of FIG. 7 includes one or more exemplary spines 700, however, the embodiment shown in FIG. 7 includes one such spine 700. The spine structure 700 is positioned internally within the apparatus 100 and includes a solid or hollow cross-sectional geometry. The solid or hollow cross-sectional geometry may include, but is not limited to, an ellipse, a circle, a triangle, a rounded triangle, a quadrilateral, a rounded quadrilateral, a rectangle, a rounded rectangle, a square, a rounded square, a trapezoid, a rounded trapezoid, a parallelogram, a rounded parallelogram, a rhombus, a rounded rhombus, a pentagon, a rounded pentagon, a star, a rounded star, or combinations thereof. Further, the spine 700 may be made of any suitable material, including, but not limited to, a metal, a plastic, an acrylonitrile butadiene styrene (ABS), a polylactic acid (PLA), an acetal, a polyamide, an acrylic, a polycarbonate, a polyurethane, or combinations thereof.

Figure 8:
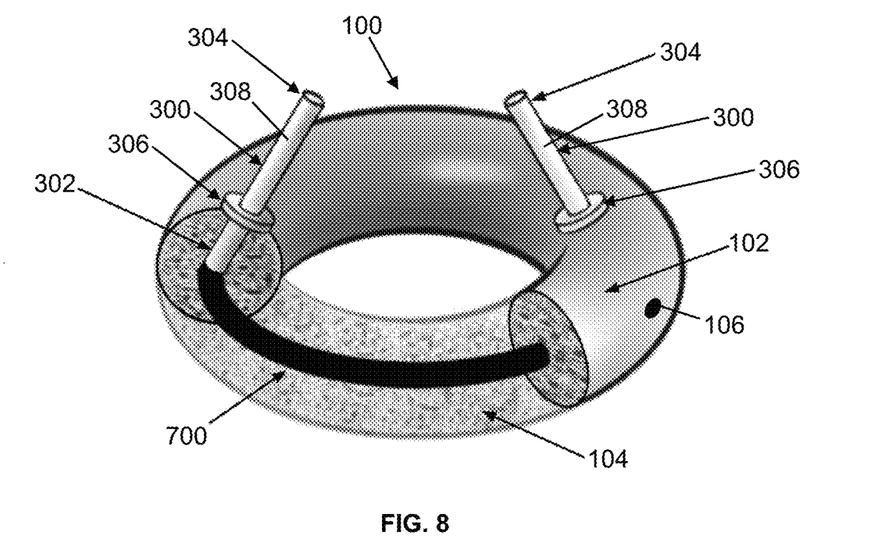
FIG. 8 is a rendered cutaway view of another exemplary closed loop granular jamming apparatus which includes a compliant spine and articulating inserts, according to an embodiment of the present disclosure.

Referring now to FIG. 8, a rendered cutaway view of another exemplary closed loop granular jamming apparatus 100 is shown, which includes a compliant spine 700 and articulating inserts 300. The general embodiments of the membranes 102 are shown in FIG. 4, with the addition of at least one insert 300 including a proximal end 302 and a distal end 304, wherein the proximal end 302 is positioned internal of the apparatus membrane 102 and surrounded circumferentially by granules 104, and the distal end 104 is located external of the apparatus membrane 102 and is exposed to the ambient environment, and the general embodiment of the compliant spine structure 700 is shown in FIG. 7. The proximal end 302 of the exemplary insert 300 is either coupled to or disjointed from the compliant spine structure 700.

Figure 9:
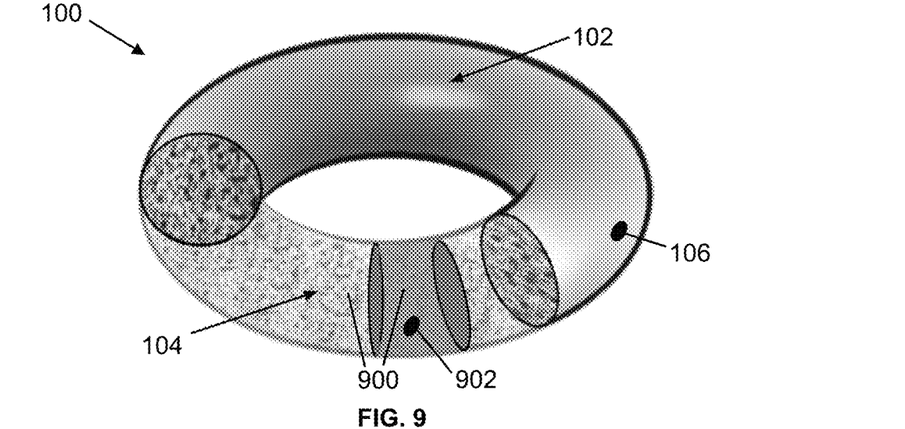
FIG. 9 is a rendered cutaway view of an exemplary closed loop granular jamming apparatus including a plurality of individual internal fluid chambers, according to an embodiment of the present disclosure.

Referring to FIG. 9, in one additional set of embodiments, the membrane 102 surrounds a plurality of individual internal fluid chambers 900, the granular material 104 is deposited within each of the plurality of individual fluid chambers 900, and each of the plurality of individual fluid chambers 900 is arranged and disposed for fluid egress and ingress. In one embodiment (not shown), at least two of the plurality of individual fluid chambers 900 are connected by a passage for fluid egress and ingress. In another embodiment (FIG. 9) at least one of the plurality of individual fluid chambers 900 is disconnected from the remainder of the plurality of individual fluid chambers 900 for fluid egress and ingress and includes a separate port 902 for fluid egress and ingress.

Figure 10:
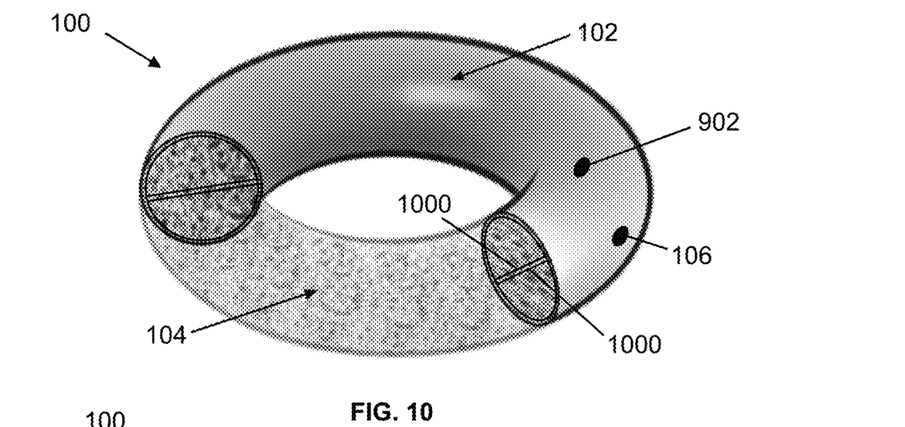
FIG. 10 is a rendered cutaway view of an exemplary closed loop granular jamming apparatus including at least one additional membrane in a stacked arrangement with a first membrane, according to an embodiment of the present disclosure.
Figure 11:
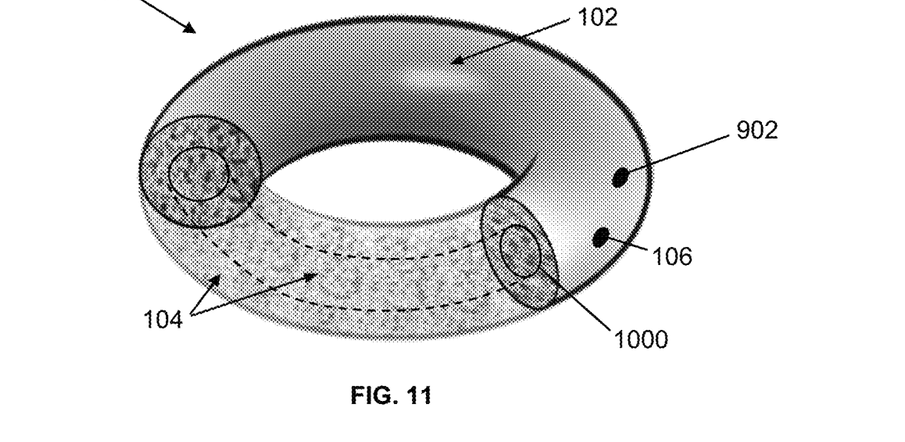
FIG. 11 is a rendered cutaway view of an exemplary closed loop granular jamming apparatus including at least one additional membrane disposed within a first membrane, according to an embodiment of the present disclosure.

Referring to FIGS. 10 and 11, in one additional set of embodiments the apparatus 100 further includes at least one additional membrane 1000 fashioned in a three-dimensional, closed loop geometry which is mathematically defined by a genus g surface where g is greater than or equal to one, wherein the granular material 104 is deposited within at least one additional enclosed space of the at least one additional membrane 1000, and at least one additional port 902 provides a source of fluid egress and ingress from and to the at least one additional enclosed space, wherein the membrane 102 and the at least one additional membrane 1000 are disposed in a vertical stacked configuration (FIG. 10) and constrained relative to one another via straps, adhesive, an outer membrane, or combinations thereof, or the at least one additional membrane 1000 is disposed within the membrane 102 (FIG. 11). In one embodiment the membrane 102 and the at least one additional membrane are connected by a passage for fluid egress and ingress (not shown). In another embodiment, the membrane 102 and the at least one additional membrane are disconnected from one another for fluid egress and ingress (FIGS. 10 and 11).

All of the features previously stated and shown in FIGS. 1-11 may be combined with one another in any suitable combination. For example, such embodiments include a closed loop granular jamming apparatus 100 with multiple chambers and inserts 300, and an embodiment including a closed loop granular jamming apparatus 100 with stack bodies and spines 700.

Figure 12:
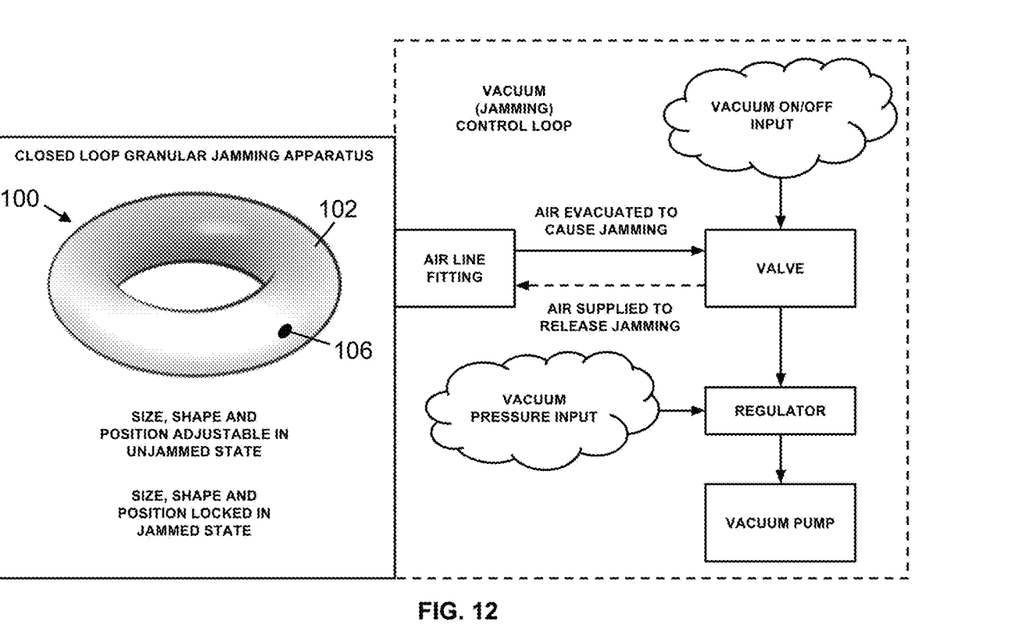
FIG. 12 is a diagrammatic view of a closed loop granular jamming system, including the closed loop granular jamming apparatus of FIG. 1 and a control system, according to an embodiment of the present disclosure.

Referring now to FIG. 12, a diagrammatic view of a closed loop granular jamming system is shown, including the closed loop granular jamming apparatus 100 of FIG. 1 and a control system. The control system activates, maintains, and deactivates jamming of the apparatus 100. The user may toggle the apparatus 100 between jammed and unjammed states. In the jammed state, the apparatus 100 is rigid, and the size, shape, and position of the body are locked. In the unjammed state, the apparatus 100 is deformable, and the size, shape, and position of the body are adjustable. The apparatus 100 is activated to a jammed state by the evacuation of fluid from within the membrane structure 102. The working fluid, for example air, is evacuated from the apparatus 100 via negative (vacuum) pressure. The amount of vacuum pressure is specified as a user input to the system and controlled via a fluid regulator. The vacuum pressure supply is determined by user input to a toggle (on/off) valve. The working fluid may be transmitted via tubing, which connects the granular jamming apparatus 100 to the valve, the valve to the regulator, and the regulator to the vacuum pump. Such tubing connects to the novel granular jamming apparatus 100 via a fitting or port 106 for fluid ingress or egress.

In one embodiment, a method for reversibly manipulating a body includes contacting the body with a closed loop granular jamming apparatus in a deformable, unjammed state, manipulating the closed loop granular jamming apparatus to a desired conformation in contact with and relative to the body, and at least partially evacuating a fluid from within the membrane through the port to place the closed loop granular jamming apparatus in a rigid, jammed state. In the jammed state, the closed loop granular jamming apparatus retracts an opening in the body, retains an opening in the body, holds the body, clamps the body, or combinations thereof, while permitting increased visibility and access to an area adjacent to the closed loop granular jamming apparatus relative to a comparative jamming apparatus which is identical to the closed loop granular jamming apparatus except that the comparative jamming apparatus has a comparative membrane fashioned in a comparative three-dimensional, closed loop geometry which is mathematically defined by a comparative genus g surface where g is equal to zero. The body may be an article, tissue, an organ, an instrument, or combinations thereof. The area adjacent to the closed loop granular jamming apparatus may be a surgical site, a work space, the inner workings of a component or mechanical device, or combinations thereof.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. All features described above in isolation are understood and intended to be combinable with one another in various combinations as would be understood by a person having ordinary skill in the art, unless specified to the contrary.

What is claimed is:

1. A closed loop granular jamming apparatus comprising:
   a membrane fashioned in a three-dimensional, closed loop geometry which is mathematically defined by a genus g surface where g is greater than or equal to one;
   a granular material deposited within an enclosed space of the membrane;
   a port providing a source of fluid egress and ingress from and to the enclosed space; and
   at least one insert including a proximal end and a distal end,
   wherein the proximal end is disposed within the apparatus membrane and is surrounded circumferentially by the granular material, and the distal end is disposed outside of the apparatus membrane and is exposed to an ambient environment.

2. The apparatus of claim 1, wherein the membrane fashioned is made of an elastomeric material, a polymer, a polyester film, a coated cloth, or combinations thereof.

3. The apparatus of claim 1, wherein the granular material includes small granules of an organic solid compound, and inorganic solid compound, or a mixture of the organic solid compound and the inorganic solid compound.

4. The apparatus of claim 3, wherein the compound includes a material selected from the group consisting of plastic materials, metal materials, glass materials, wood materials, coffee materials, nut materials, seed materials, and combinations thereof.

5. The apparatus of claim 1, wherein the proximal end includes a shaft and a cross-sectional geometry selected from the group consisting of an ellipse, a circle, a triangle, a rounded triangle, a quadrilateral, a rounded quadrilateral, a rectangle, a rounded rectangle, a square, a rounded square, a trapezoid, a rounded trapezoid, a parallelogram, a rounded parallelogram, a rhombus, a rounded rhombus, a pentagon, a rounded pentagon, a star, a rounded star, and combinations thereof.

6. The apparatus of claim 1, wherein the proximal end includes a shaft and a three-dimensional geometry selected from the group consisting of a cylinder, a right cylinder, an oblique cylinder, a circular cylinder, an elliptical cylinder, a triangular prism, a rounded triangular prism, a rectangular prism, a rounded rectangular prism, a spheroid, a sphere, a finned shaft, a screw, and combinations thereof.

7. The apparatus of claim 1, wherein the distal end includes a shaft and a cross-sectional geometry selected from the group consisting of an ellipse, a circle, a triangle, a rounded triangle, a quadrilateral, a rounded quadrilateral, a rectangle, a rounded rectangle, a square, a rounded square, a trapezoid, a rounded trapezoid, a parallelogram, a rounded parallelogram, a rhombus, a rounded rhombus, a pentagon, a rounded pentagon, a star, a rounded star, and combinations thereof.

8. The apparatus of claim 1, wherein the distal end includes a shaft and a three-dimensional geometry of one of a tapered shaft, spatula, flat blade retractor, sharp finger retractor, a blunt finger retractor, and combinations thereof.

9. The apparatus of claim 1, wherein the insert includes a material composition selected from the group consisting of a metal, a plastic, an acrylonitrile butadiene styrene (ABS), a polylactic acid (PLA), an acetal, a polyamide, an acrylic, a polycarbonate, a polyurethane, and combinations thereof.

10. The apparatus of claim 1, wherein the insert is of modular construction such that the proximal end is removable and replaceable by a twist lock, screw, snap fit, magnet, or combinations thereof.

11. The apparatus of claim 1, wherein the insert is coupled to the membrane by an evacuable sealing relationship such that the membrane is molded around the insert or the insert is connected to the membrane via a seal or a gasket.

12. A closed loop granular jamming apparatus comprising:
    a membrane fashioned in a three-dimensional, closed loop geometry which is mathematically defined by a genus g surface where g is greater than or equal to one;
    a granular material deposited within an enclosed space of the membrane;
    a port providing a source of fluid egress and ingress from and to the enclosed space; and
    a compliant spine structure disposed internally within the apparatus and surrounded circumferentially by the granular material.

13. The apparatus of claim 12, wherein the spine structure includes a material composition selected from the group consisting of a metal, a plastic, an acrylonitrile butadiene styrene (ABS), a polylactic acid (PLA), an acetal, a polyamide, an acrylic, a polycarbonate, a polyurethane, and combinations thereof.

14. The apparatus of claim 12, wherein the spine structure includes a three-dimensional, closed loop geometry which is mathematically defined by a genus g surface where g is equal to that of the apparatus.

15. The apparatus of claim 12, wherein the spine structure includes a solid or hollow cross-sectional geometry selected from the group consisting of an ellipse, a circle, a triangle, a rounded triangle, a quadrilateral, a rounded quadrilateral, a rectangle, a rounded rectangle, a square, a rounded square, a trapezoid, a rounded trapezoid, a parallelogram, a rounded parallelogram, a rhombus, a rounded rhombus, a pentagon, a rounded pentagon, a star, a rounded star, and combinations thereof.

16. The apparatus of claim 12, further comprising at least one insert including a proximal end and a distal end, wherein the proximal end is disposed within the apparatus membrane and is surrounded circumferentially by the granular material, and the distal end is disposed outside of the apparatus membrane and is exposed to an ambient environment.

17. The apparatus of claim 16, wherein the proximal end is coupled to the compliant spine structure.

18. The apparatus of claim 16, wherein the proximal end is disjointed from the compliant spine structure.

19. A closed loop granular jamming apparatus comprising:
    a membrane fashioned in a three-dimensional, closed loop geometry which is mathematically defined by a genus g surface where g is greater than or equal to one;
    a granular material deposited within an enclosed space of the membrane; and
    a port providing a source of fluid egress and ingress from and to the enclosed space,
    wherein the membrane surrounds a plurality of individual internal fluid chambers, the granular material is deposited within each of the plurality of individual fluid chambers, and each of the plurality of individual fluid chambers is arranged and disposed for fluid egress and ingress.

20. The apparatus of claim 19, wherein at least two of the plurality of individual fluid chambers are connected by a passage for fluid egress and ingress.

21. The apparatus of claim 19, wherein at least one of the plurality of individual fluid chambers is disconnected from the remainder of the plurality of individual fluid chambers for fluid egress and ingress and includes a separate port for fluid egress and ingress.

22. A closed loop granular jamming apparatus comprising:
    a membrane fashioned in a three-dimensional, closed loop geometry which is mathematically defined by a genus g surface where g is greater than or equal to one;
    a granular material deposited within an enclosed space of the membrane;
    a port providing a source of fluid egress and ingress from and to the enclosed space;
    at least one additional membrane fashioned in a three-dimensional, closed loop geometry which is mathematically defined by a genus g surface where g is greater than or equal to one;
    the granular material being deposited within at least one additional enclosed space of the at least one additional membrane; and
    at least one additional port providing a source of fluid egress and ingress from and to the at least one additional enclosed space,
    wherein the membrane and the at least one additional membrane are disposed in a vertical stacked configuration and constrained relative to one another via straps, adhesive, an outer membrane, or combinations thereof.

23. The apparatus of claim 22, wherein the membrane and the at least one additional membrane are connected by a passage for fluid egress and ingress.

24. A method for reversibly manipulating a body, comprising:
    contacting the body with a closed loop granular jamming apparatus in a deformable, unjammed state, wherein the closed loop granular jamming apparatus includes:
        a membrane fashioned in a three-dimensional, closed loop geometry which is mathematically defined by a genus g surface where g is greater than or equal to one;
        a granular material deposited within an enclosed space of the membrane;
        a port providing a source of fluid egress and ingress from and to the enclosed space; and
        at least one insert including a proximal end and a distal end;
    manipulating the closed loop granular jamming apparatus to a desired conformation in contact with and relative to the body; and
    at least partially evacuating a fluid from within the membrane through the port to place the closed loop granular jamming apparatus in a rigid, jammed state,
    wherein the proximal end is disposed within the apparatus membrane and is surrounded circumferentially by the granular material, and the distal end is disposed outside of the apparatus membrane and is exposed to an ambient environment, and
    wherein in the jammed state, the closed loop granular jamming apparatus retracts an opening in the body, retains an opening in the body, holds the body, clamps the body, or combinations thereof, while permitting increased visibility and access to an area adjacent to the closed loop granular jamming apparatus relative to a comparative jamming apparatus which is identical to the closed loop granular jamming apparatus except that the comparative jamming apparatus has a comparative membrane fashioned in a comparative three-dimensional, closed loop geometry which is mathematically defined by a comparative genus g surface where g is equal to zero.

\* \* \* \* \*